United States Patent [19]

Pearson et al.

[11] 4,009,151
[45] Feb. 22, 1977

[54] POLYMERS OF 2-VINYL-FLUORENONE AND DERIVATIVES THEREOF

[75] Inventors: James M. Pearson, Webster; John F. Yanus, Fairport, both of N.Y.

[73] Assignee: Xerox Corporation, Stamford, Conn.

[22] Filed: Oct. 30, 1975

[21] Appl. No.: 627,167

Related U.S. Application Data

[60] Continuation of Ser. No. 494,014, Aug. 1, 1974, abandoned, which is a division of Ser. No. 411,577, Oct. 31, 1973.

[52] U.S. Cl. .................... 260/63 K; 260/63 BB; 260/66; 260/590 D
[51] Int. Cl.$^2$ .................... C08G 2/16; C08G 2/18
[58] Field of Search .............. 260/63 K, 66, 63 BB, 260/590

[56] References Cited

UNITED STATES PATENTS 3,370,045  2/1968  Baer .................................... 260/63

OTHER PUBLICATIONS

Braun, J. Polymer Science, Part C, 1967 Pub. 1968 No. 24 pp. 7–13.

*Primary Examiner*—Carman J. Seccuro
*Attorney, Agent, or Firm*—James J. Ralabate; James Paul O'Sullivan; Jerome L. Jeffers

[57] ABSTRACT

Disclosed is a composition of matter characterized by the structural formula:

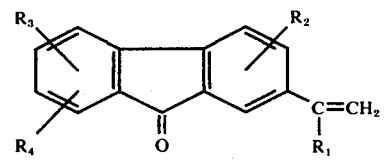

wherein $R_1$ is hydrogen or methyl and $R_2$, $R_3$ and $R_4$ are hydrogen, halogen or aliphatic groups containing 1 to 4 carbon atoms. Also disclosed are vinyl polymers of the above compounds.

5 Claims, No Drawings

POLYMERS OF 2-VINYL-FLUORENONE AND DERIVATIVES THEREOF

This is a continuation of application Ser. No. 494,014, filed Aug. 1, 1974, now abandoned, which application was a divisional of application Ser. No. 411,577 filed on Oct. 31, 1973.

BACKGROUND OF THE INVENTION

Fluorenone and 2-vinylfluorene are known compounds. However, the oxidation of 2-vinylfluorene to 2-vinylfluorenone is problematical due to the reaction of the vinyl group during oxidation. In order to convert 2-vinylfluorene to 2-vinylfluorenone it is necessary to employ an oxidant which is sufficiently strong to cause the desired oxidation without causing prepolymerization or other undesirable side reactions.

Preparation of 2-vinylfluorenone would be desirable since it can be polymerized to provide poly-2-vinylfluorenone. This polymer is of interest since it has been found to be an excellent insulator which can be applied to conductive substrates from solution. The monomers themselves possess this insulating property; however, it is preferred to polymerize the monomer before its application to the substrate or to cause polymerization in situ after such application due to the enhanced mechanical properties of the polymer film as compared to a film of the monomer. However, the inability of the prior art to come up with a method to prepare 2-vinylfluorenone has hindered attempts to prepare the polymer. An alternate route for preparation of the polymer, i.e. preparation of poly-2-vinylfluorene with subsequent oxidation of the fluorene units to fluorenone, has not been entirely successful. For example, it is reported in Polymer Letters, Vol. 9, pp. 671–676 (1971) that a 50/50 copolymer of 2-vinylfluorene/2-vinylfluorenone can be prepared by the oxidation of poly-2-vinylfluorene with chromium trioxide in glacial acetic acid. This reference illustrates the difficulty of obtaining complete oxidation by pointing out that a residue having an oxygen analysis indicating almost complete conversion to poly-2-vinylfluorenone was insoluble in organic solvents and strong acids. This insolubility, which is probably due to extensive crosslinking during the oxidation, is undesirable since the polymers cannot be applied to substrates from their solutions in organic solvents. It appears, from the state of the art, that the only way to prepare poly-2-vinylfluorenone containing no fluorene units in a form which is soluble in common organic solvents is to prepare 2-vinylfluorenone and cause its polymerization.

Accordingly, it would be desirable and it is an object of the present invention to provide a method for the preparation of 2-vinylfluorenone.

An additional object is to provide, as a composition of matter, 2-vinylfluorenone, α-methyl-2-vinylfluorenone and substituted derivatives thereof.

An additional object is to provide polymers of 2-vinylfluorenone and α-methyl-2-vinylfluorenone.

A further object is to provide copolymers of 2-vinylfluorenone with other vinyl monomers.

SUMMARY OF THE INVENTION

The present invention is a composition of matter characterized by the structural formula:

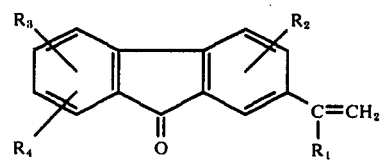

In the above formula $R_1$ is hydrogen or methyl and $R_2$, $R_3$ and $R_4$ are hydrogen, halogen or aliphatic groups containing 1 to 4 carbon atoms.

The above-described composition is prepared by reacting a composition of the formula:

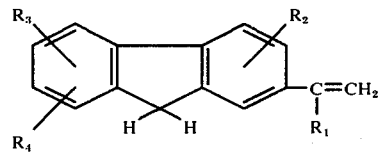

wherein $R_1$, $R_2$, $R_3$ and $R_4$ are as defined above with benzyltrimethyl ammonium hydroxide and oxygen in a suitable solvent to oxidize the fluorene to fluorenone.

DETAILED DESCRIPTION

The novel compounds of the present invention are characterized by the formula:

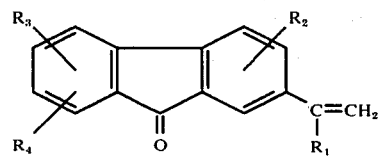

In the above formula, $R_1$ is H or methyl. The remaining constituents, i.e. $R_2$, $R_3$ and $R_4$ are either H, halogen or aliphatic groups having from 1 to 4 carbon atoms. Examples of $R_2$, $R_3$ and $R_4$ include alkyl or substituted alkyl, e.g. methyl, ethyl, chloroethyl, cyanoethyl, propyl, butyl and isobutyl. In addition, the $R_2$, $R_3$ and $R_4$ substituents can be halogen; e.g. bromo, chloro or fluoro; or alkoxy; e.g. methoxy, ethoxy, propoxy or butoxy. In general, the composition in which the R substituents are H, i.e. 2-vinyl fluorenone, is preferred.

These compositions are prepared by the controlled oxidation of 2-vinylfluorene. Great care must be taken in selecting an oxidant that is neither too mild nor too strong. Too mild an oxidant will not convert the fluorene to fluorenone, whereas too strong an oxidant will cause premature polymerization or oxidative reactions of the vinyl substituent. It has been discovered that 2-vinylfluorenone can be prepared in good yields without appreciable polymerization by reacting, in a suitable solvent, 2-vinylfluorene with benzyltrimethyl ammonium hydroxide and oxygen. This process can also be used to prepare the derivatives of 2-vinylfluorenone and α-methyl-2-vinylfluorenone described above.

After preparation, the 2-vinylfluorenone or derivative thereof can be polymerized either by bulk or solution polymerization or emulsion techniques to provide homopolymeric compositions consisting of repeating units of -2-vinylfluorenone or derivatives thereof characterized by the formula:

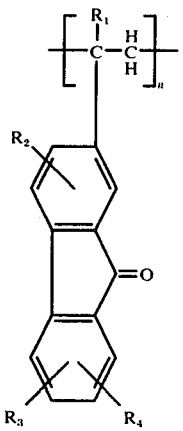

where $R_1$, $R_2$, $R_3$ and $R_4$ are as defined above and $n$ is a number representing the degree of polymerization.

This polymerization, which can be initiated either by free radical or cationic initiators, can also be used to provide copolymers of 2-vinylfluorenone and other vinyl monomers. Examples of other vinyl monomers which may be copolymerized with 2-vinylfluorenone include styrene, vinyl chloride, methyl methacrylate, vinyl carbazole, vinyl naphthalene, methyl acrylate, isoprene, butadiene, substituted styrenes, acrylonitrile and vinyl acetate.

The degree of polymerization which can be obtained will vary depending on the polymerization technique. Generally, a degree of polymerization of up to 1000 may readily be obtained and higher degrees of polymerization are possible. A degree of polymerization of from 10 to 5000 is typical.

The invention is further illustrated by the following examples in which all percentages are by weight unless otherwise specified.

EXAMPLE I

Synthesis of 2-vinylfluorene is carried out as follows:

Triphenylmethyl phosphonium bromide (36 gms/0.1 mole) in 500 milliliters of dry THF is treated under nitrogen with 90 milliliters of a 1.1 molar solution of n-butyl lithium in hexane and stirred for 2 hours. A solution of 19.4 gms. (0.1 mole) of fluorene-2-carboxaldehyde in 100 milliliters of THF is added dropwise and the final mixture refluxed for 1 1/2 hours. One liter of hexane is added to the cold solution and the precipitate filtered off. The filtrate is evaporated and the residue chromatographed on alumina (Woehlm neutral) using hexane to give 15 gms. (75% theory) of product. Recrystallization from hexane yields 2-vinylfluorene as colorless plates. The structure of the product is confirmed by nuclear magnetic resonance and elemental analysis.

EXAMPLE II

Synthesis of 2-vinylfluorenone is accomplished as follows:

The 2-vinylfluorene prepared in Example I is dissolved in 800 milliliters of pyridine and cooled to 0° C. One-half milliliter of a 40% solution of benzyltrimethyl ammonium hydroxide in pyridine is slowly added with air being bubbled through the reaction solution. The initially formed red coloration fades over a period of 1 to 2 hours and the solution is poured into water and extracted with benzene to yield 9 grams (90% theory) of a yellow solid. The residue is chromatographed on alumina (Woehlm basic) and eluted with benzene. Recrystallization from hexane gives 2-vinylfluorenone as a pale yellow material (melting point 69°-70° C). The structure of the product is confirmed by nuclear magnetic resonance and elemental analysis.

EXAMPLE III

Synthesis of α-methyl-2-vinylfluorenone is accomplished by acetylation of fluorene as described in Organic Synthesis, Collective, Vol. 3, page 23. Conversion to the vinyl derivative is achieved in a 70% yield using the procedure described in Example I. Recrystallization of the product from hexane gives α-methyl-2-vinylfluorene as tan crystals (m.p. 155°-156° C). The product is oxidized to the corresponding fluorenone derivative by the procedure described in Example II. Recrystallization of the product from hexane yields α-methyl-2-vinylfluorenone as pale yellow crystals (m.p. 76°-77° C). The structure of the product is verified by nuclear magnetic resonance and elemental analysis.

Polymerization of 2-vinylfluorenone is accomplished in following Examples IV – VII.

EXAMPLE IV

Emulsion

In a 1 liter Morton flask is placed 200 milliliters of $H_2O$ together with 3 gms. of sodium oleate. The solution is blanketed with nitrogen and heated to 80°-85° C. At this point, 13.4 gm. (0.065 moles) of 2-vinylfluorenone are added to the flask. Subsequently, three portions of a solution of 0.01 gm. of $K_2S_2O_8$ in 10 milliliters of $H_2O$ are added over a period of 1 hour. The resulting solution is allowed to stir for 6 hours and coagulated with 50 milliliters of a saturated sodium acetate solution. The resulting precipitate is filtered and dried to yield 11.5 gm. of a polymer having a molecular weight of approximately 350,000.

EXAMPLE V

Cationic

In a beverage bottle are placed 5 gm. (0.024 M) of 2-vinylfluorenone and 75 milliliters of methylene chloride to form a solution which is saturated with nitrogen. The bottle is capped and chilled to −30° C whereupon 0.10 milliliter of a $BF_3 \cdot Et_2O$ solution is added as catalyst and the mixture stirred for 3 hours. The mixture is then quenched with methanol to yield 3 gm. of a polymer having a molecular weight of approximately 10,000.

EXAMPLE VI

Solution

In a polymer tube are placed 0.5 gm. (0.0024 M) 2-vinylfluorenone; 0.007 gm. ($4 \times 10^{-5}$M) of AIBN and 15 milliliters of toluene. The tube is degassed, sealed and heated to 85° C for 24 hours. The reaction product is dissolved in THF and precipitated with methanol to yield 0.35 gm. of a polymer having a molecular weight of approximately 50,000.

EXAMPLE VII
Bulk

In a 100 milliliter round bottomed flask are placed 11.1 gm. (0.05 M) 2-vinylfluorenone and 0.005 gm. (3 × 10⁻⁵ M) of AIBN. The contents are blanketed with nitrogen and heated to 70°–75° C for 2 hours. The reaction product is dissolved in THF and precipitated in benzene to yield 8 gm. of a polymer having a molecular weight of approximately 200,000.

EXAMPLE VIII

Cationic polymerization of α-methyl-2-vinylfluorenone.

In a 100 milliliter flask are placed 2 gm. of α-methyl-2-vinylfluorenone and 50 milliliters of chlorobenzene. The contents of the flask are blanketed with nitrogen and cooled to −40° C at which point a small amount of BF₃ gas is added. The reaction mass, which turned red upon the addition of the BF₃, is kept below −30° C with stirring for 3 hours. The reaction is quenched with methanol and precipitated with methanol to yield 0.5 gm. of a polymer having a molecular weight of approximately 10,000.

EXAMPLE IX

A copolymer of 2-vinylfluorenone and N-vinylcarbazole is prepared as follows:

In a polymer tube are placed 1.1 gm. (0.005 M) of 2-vinylfluorenone; 0.95 gm. (0.005 M) of N-vinylcarbazole; 5 milliliters of benzene and 0.048 gm. (2 × 10⁻⁴ M) benzoyl peroxide. The tube is degassed, sealed and heated to 65° C for 18 hours. The resulting product is precipitated into methanol to give an eighty percent yield of a copolymer containing approximately 80 mole % of 2-vinylfluorenone and 20 mole % of N-vinylcarbazole.

The polymers of the instant invention possess excellent dielectric and insulating properties making them ideal materials for use in thin polymer film capacitors. Furthermore, the polymers exhibit good thermal stability at elevated temperatures up to 150° C. The polymers possess dielectric constants of approximately 4(100 Hz) over the temperature range of −200° C to 50° C with a dielectric loss factor of less than 0.1 at the same frequency.

The polymers can be used to fabricate capacitors using either solvent coating or in situ polymerization techniques.

EXAMPLE X

A solution of poly-2-vinylfluorenone is prepared by dissolving the polymer in benzene. The solution is coated on a thin aluminum film using a doctor blade technique and the solvent evaporated to provide a polymer film approximately 2.5 μ thick.

This metal/insulator sheet is cut into units of the desired dimensions two of which are positioned so as to allow contact leads to be attached, rolled into a compact cylinder and potted in an epoxy type resin to produce a functioning capacitor.

EXAMPLE XI

A standard paper/aluminum foil capacitor is impregnated with a solution of 2-vinylfluorenone and AIBN in benzene. The monomer is polymerized using heat as the stimulus and potted as previously described to provide the finished capacitor.

What is claimed is:

1. A homopolymeric composition consisting of repeating units characterized by the structural formula:

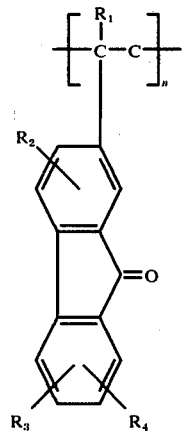

wherein $R_1$ is hydrogen or methyl, $R_2$, $R_3$ and $R_4$ are hydrogen or aliphatic groups containing from 1 to 4 carbon atoms and $n$ is a number representing the degree of polymerization.

2. The polymeric composition of claim 1 wherein $n$ is a number within the range of 10 to 5,000.

3. The polymeric composition of claim 1 wherein $R_2$, $R_3$, and $R_4$ are H.

4. The polymeric composition of claim 3 in which $R_1$ is H.

5. A copolymeric composition consisting of units characterized by the structural formula:

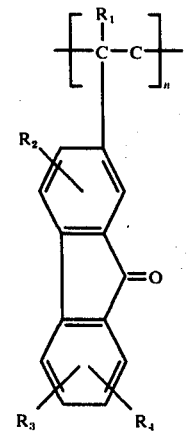

wherein $R_1$ is hydrogen or methyl, $R_2$ $R_3$ and $R_4$ are hydrogen or aliphatic groups containing from 1 to 4 carbon atoms and N is a number representing the degree of polymerization which are copolymerized with another vinyl monomer selected from the group consisting of styrene, vinyl chloride, methyl methacrylate, vinyl carbazole, vinyl naphthalene, isoprene, butadiene, a substituted styrene, acrylonitrile, vinyl pyridine and vinyl acetate.

* * * * *